United States Patent
Trejo O'Reilly et al.

(10) Patent No.: US 9,809,692 B2
(45) Date of Patent: Nov. 7, 2017

(54) CATALYST RESIN

(71) Applicant: Rohm and Haas Company, Philadelphia, PA (US)

(72) Inventors: Jose Antonio Trejo O'Reilly, Lansdale, PA (US); Takashi Masudo, Natori (JP); Daika Kouzaki, Iwanuma (JP)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 15/300,335

(22) PCT Filed: Apr. 9, 2015

(86) PCT No.: PCT/US2015/025172
§ 371 (c)(1),
(2) Date: Sep. 29, 2016

(87) PCT Pub. No.: WO2015/157552
PCT Pub. Date: Oct. 15, 2015

(65) Prior Publication Data
US 2017/0183473 A1    Jun. 29, 2017

Related U.S. Application Data

(60) Provisional application No. 61/977,369, filed on Apr. 9, 2014.

(51) Int. Cl.
| | | |
|---|---|---|
| *C07C 67/08* | (2006.01) |
| *B01J 31/06* | (2006.01) |
| *C08J 9/20* | (2006.01) |
| *C08J 9/14* | (2006.01) |

(52) U.S. Cl.
CPC ............ *C08J 9/20* (2013.01); *B01J 31/06* (2013.01); *C07C 67/08* (2013.01); *C08J 9/142* (2013.01); *C08J 2325/08* (2013.01)

(58) Field of Classification Search
CPC ............ C07C 67/08; B01J 31/06; B01J 31/10
See application file for complete search history.

(56) References Cited

U.S. PATENT DOCUMENTS

| | | | |
|---|---|---|---|
| 4,792,620 A | * | 12/1988 | Paulik ............... B01J 31/0231 560/232 |
| 5,804,606 A | | 9/1998 | Surowiec et al. |
| 5,866,713 A | | 2/1999 | Suzuki et al. |
| 2003/0189005 A1 | | 10/2003 | Inoue et al. |

FOREIGN PATENT DOCUMENTS

| | | |
|---|---|---|
| EP | 0417407 A1 | 3/1991 |
| EP | 0417407 B1 * | 5/1994 |
| GB | 1020907 A | 2/1966 |
| JP | 53-034893 B2 | 3/1978 |

OTHER PUBLICATIONS

Zaragoza Dorwald, Side Reactions in Organic Synthesis, 2005, Wiley-VCH Verlag GmbH & Co. KGaA, Weinheim, Preface. p. IX.*
Norskov et al, Nature Chemistry, Towards the Computational Design of Solid Catalysts, 2009, 1, pp. 37-46.*
Howdle, et al., "Reversibly collapsible macroporous poly(styrene-divinylbenzene) resins," Polymer, vol. 41, 2000, pp. 7273-7277.

* cited by examiner

*Primary Examiner* — Paul A Zucker
(74) *Attorney, Agent, or Firm* — Carl P. Hemenway

(57) ABSTRACT

Provided is a plurality of resin beads, wherein the resin beads comprise polymerized units of monovinyl aromatic monomer and polymerized units of multivinyl aromatic monomer, and wherein the resin beads have BET surface area of 15 to 38 m²/g and volume capacity of 0.7 or higher. Also provided is a method of making a product of the chemical reaction of one or more reactants, where the method comprises reacting the reactants with each other in the presence of such resin beads.

9 Claims, No Drawings

CATALYST RESIN

One method of preparing an alkyl ester of (meth)acrylic acid is to react (meth)acrylic acid with an alkyl alcohol in the presence of a catalyst. Some useful catalysts are strongly acidic cation exchange resins ("SAC resins"). Historically, SAC resins have been available as one of two types: gel resins or macroporous resins. Historically, typical gel resins were made without the use of porogen and are made with relatively low level of crosslinking; while they tended to be effective when used as catalysts, they tended to have poor physical toughness. Historically, typical macroporous resins were made with porogen and with relatively high level of crosslinking; they tended to be less effective when used as catalysts, but they tended to have good physical toughness. Thus, in the past, when a catalyst was desired, it was necessary to choose between gel resins and macroporous resins; that is, it was necessary to sacrifice either catalytic effectiveness or physical toughness.

U.S. Pat. No. 5,866,713 discloses a method of preparing a (meth)acrylic acid ester. The method of U.S. Pat. No. 5,866,713 involves reacting (meth)acrylic acid with a $C_{1-3}$ alcohol in the presence of a strongly acidic ion exchange resin. None of the resins disclosed by U.S. Pat. No. 5,866,713 has both a high level of catalytic effectiveness and a high level of physical strength. It is desired to provide a resin that has both a high level of catalytic effectiveness and a high level of physical strength.

The following is a statement of the invention.

A first aspect of the present invention is a method of making a plurality of resin beads comprising
  (a) providing a reaction mixture comprising monovinyl aromatic monomer, multivinyl aromatic monomer, and porogen, wherein
    (i) the amount of said monovinyl aromatic monomer is 93% to 96% by weight based on the weight of said monovinyl aromatic monomer plus the weight of said multivinyl aromatic monomer,
    (ii) the amount of said multivinyl aromatic monomer is 4% to 6.5% by weight based on the weight of said monovinyl aromatic monomer plus the weight of said multivinyl aromatic monomer,
    (iii) the amount of porogen is 34.5% to 39% by weight based on the weight of said monovinyl aromatic monomer plus the weight of said multivinyl aromatic monomer,
  (b) performing aqueous suspension polymerization on said reaction mixture to form resin beads, and
  (c) sulfonating said resin beads.

A second aspect of the present invention is a plurality of resin beads made by the method of the first aspect.

A the third aspect of the present invention is a plurality of resin beads, wherein said resin beads comprise
  (i) 93% to 96% polymerized units of monovinyl aromatic monomer, by weight based on the weight of said resin beads,
  (ii) 4% to 7% polymerized units of multivinyl aromatic monomer, by weight based on the weight of said resin beads,
wherein said resin beads have BET surface area of 15 to 38 $m^2/g$ and volume capacity of 0.7 or higher.

A fourth aspect of the present invention is a method of making a product of a chemical reaction of one or more reactants, said method comprising reacting said one or more reactants with each other in the presence of the plurality of resin beads of the second aspect or the third aspect.

The following is a detailed description of the invention.

As used herein, the following terms have the designated definitions, unless the context clearly indicates otherwise.

"Resin" as used herein is a synonym for "polymer." A "polymer," as used herein is a relatively large molecule made up of the reaction products of smaller chemical repeat units. Polymers may have structures that are linear, branched, star shaped, looped, hyperbranched, crosslinked, or a combination thereof; polymers may have a single type of repeat unit ("homopolymers") or they may have more than one type of repeat unit ("copolymers"). Copolymers may have the various types of repeat units arranged randomly, in sequence, in blocks, in other arrangements, or in any mixture or combination thereof.

Molecules that can react with each other to form the repeat units of a polymer are known herein as "monomers." The repeat units so formed are known herein as "polymerized units" of the monomer.

Vinyl monomers have the structure

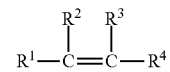

where each of $R^1$, $R^2$, $R^3$, and $R^4$ is, independently, a hydrogen, a halogen, an aliphatic group (such as, for example, an alkyl group), a substituted aliphatic group, an aryl group, a substituted aryl group, another substituted or unsubstituted organic group, or any combination thereof. As used herein, "(meth)acrylic" means acrylic or methacrylic; "(meth)acrylate" means acrylate or methacrylate. As used herein, vinyl aromatic monomers are monomers in which one or more of $R^1$, $R^2$, $R^3$, and $R^4$ contains one or more aromatic ring. A monovinyl aromatic monomer is a vinyl aromatic monomer that has exactly one non-aromatic carbon-carbon double bond per molecule. A multivinyl aromatic monomer is a vinyl aromatic monomer that has two or more non-aromatic carbon-carbon double bonds per molecule.

Beads are particles of material. Beads are spherical or roughly spherical. The size of beads is characterized by the mean diameter on a volume basis of a collection of beads. Beads have mean diameter of 0.1 to 2 mm. Resin beads are beads in which the composition of the beads contains polymer in an amount, by weight based on the weight of the beads, of 80% or more.

Some characteristics of a collection of beads are assessed as follows. Surface area is measured by the BET (Brunauer, Emmett and Teller) method, reported as a characteristic area per unit weight of sample. Pore volume is measured by the single point adsorption method with Nitrogen as the adsorbed molecule, reported as a characteristic volume per unit weight of sample. Pore size is assessed as the average pore width (4 V/A by the BET method). Sample preparation for measuring surface area is preferably done by the following procedure: wet resin is charged into a column and solvent exchanged with sequential solvent steps: methanol followed by toluene and by isooctane; the resulting resin is vacuum dried at 35° C. to 80° C.

The Moisture Hold Capacity (MHC) is measured by wetting a specific volume of resin and removing the excess water with a Buchner funnel. After removal of excess water, the weight of the moist resin is recorded. The resin is then oven dried at 105° C. for 12 hours and the dry weight is recorded. The MHC is as calculated from the following equation:

$$MHC\ (\%) = 100 * \left[1 - \left(\frac{W_D}{W_M}\right)\right]$$

where
MHC=Moisture Hold Capacity, reported as a percent
$W_D$=Weight of dry resin (grams)
$W_M$=Weight of water removed during drying Additional characteristics of a collection of beads are assessed as follows. The Volume Capacity (Vol. Cap.) is measured by measuring a volume of resin in acid form. Protons of acid form resin are eluted with Na, and quantity of proton is determined by titration with NaOH. Calculation of the volume capacity is done with the following equation:

$$VC\left(\frac{eq}{L}\right) = \frac{10 * (V_{NaOH} - V_{Blank,NaOH}) * N_{NaOH}}{V_M}$$

and Weight Capacity (W. Cap.) is measured by dry basis of resin as in the following equation:

$$W.Cap.(eq/kg) = \frac{10 \times (V_{naOH}(ml) - V_{Blank,NaOH}(ml)) \times N_{NaOH}(eq/L)}{W_{moist}(g) \times (1 - MHC\ (\%)/100)}$$

where
VC=Volume Capacity (Vol. Cap.) (equivalents per liter (eq/L))
$V_{NaOH}$=Volume used of NaOH solution for neutralization (milliliter)
$V_{Blank,NaOH}$=Volume used of NaOH solution for neutralization a blank sample (milliliter)
$N_{NaOH}$=concentration of NaOH used for titration (eq/L)
$W_{moist}$=$W_m$=weight of the water present in the moist resin
$V_M$=Volume of moist resin (milliliter)
10 in above equation is for the case of 100 ml of sample for the titration from 1,000 ml eluant for cation exchange on the resin.

Further characteristics of a collection of beads are assessed as follows. The harmonic mean particle size (HMPS) is measured and reported by Beckman Coulter Rapid vue Particle Shape and Size Analyzer; reported in units of mm. The Shrinkage tendency (MeOH Shrink) is measured by comparing the volume change of the resin in water to the volume of resin where the water has been exchanged for methanol. A known volume of resin packed bed resin in water is exchanged by passing through several bed volumes of methanol and therefore removing the water from the resin. A total of a least 5 bed volumes of methanol are required to remove the water from within the resin structure. The final volume of the resin is recorded at the end of the solvent exchange and compared to the initial volume in water; reported in units of percent (%). The Apparent Density is measured by dewatering resin as per moisture hold capacity (MHC), weighing the resin, packing in a column and then following up flow process with water expanding the resin bed at least 40% and upon halting the water flow letting the resin to pack in the column. The final volume is recorded and the ratio weight to final volume used for calculation of the Apparent Density (g/mL) at 25° C.

A compound is considered to be insoluble in a solvent if the amount of that compound that will dissolve in 100 g of the solvent at 25° C. is 1 gram or less.

The process of the present invention involves a reaction mixture that contains (i) monovinyl aromatic monomer, (ii) multivinyl aromatic monomer, and (iii) porogen.

Preferably, the monovinyl aromatic monomer contains one or monomer that is water-insoluble. Preferred monovinyl aromatic monomers are styrene and alkyl-substituted styrenes; more preferred are styrene, alpha-methyl styrene, ethyl styrene, and mixtures thereof; more preferred is styrene. The amount of monovinyl aromatic monomer is, by weight based on the sum of the weights of monovinyl aromatic monomer and multivinyl aromatic monomer, 93.5% or more; more preferably 94% or more. The amount of monovinyl aromatic monomer is, by weight based on the sum of the weights of monovinyl aromatic monomer and multivinyl aromatic monomer, 96% or less; preferably 95.5% or less; more preferably 95% or less.

Preferably, the multivinyl aromatic monomer contains one or monomer that is water-insoluble. Preferred multivinyl aromatic monomer is divinyl benzene. The amount of multivinyl aromatic monomer is, by weight based on the sum of the weights of monovinyl aromatic monomer and multivinyl aromatic monomer, 4% or more; preferably 4.5% or more; more preferably 5% or more. The amount of multivinyl aromatic monomer is, by weight based on the sum of the weights of monovinyl aromatic monomer and multivinyl aromatic monomer, 6.5% or less; more preferably 6% or less.

The porogen is a compound that is liquid at 25° C., and that is water-insoluble. The porogen is soluble (in the amount present in the reaction mixture) at 25° C. in at the mixture of monovinyl aromatic monomer and multivinyl aromatic monomer that is present in the reaction mixture. The polymer formed by polymerization of the monovinyl aromatic monomer and the multivinyl aromatic monomer is not soluble in the porogen. Preferred porogens are $C_4$-$C_8$ alkanes, $C_4$-$C_{10}$ alkanes substituted with one or more hydroxyl groups per molecule, alkyl fatty acids, and mixtures thereof; more preferred are $C_4$-$C_{10}$ alkanes substituted with one or more hydroxyl groups per molecule; more preferred are branched $C_4$-$C_8$ alkanes substituted with exactly one hydroxyl group per molecule; most preferred is 4-methyl-2-pentanol (also called methyl isobutyl carbinol, or MIBC).

The amount of porogen, by weight based on the sum of the weights of monovinyl aromatic monomer and multivinyl aromatic monomer, is 34.5% or more; more preferably 35% or more; more preferably 35.5% or more. The amount of porogen, by weight based on the sum of the weights of monovinyl aromatic monomer and multivinyl aromatic monomer, is 39% or less; preferably 38% or less; more preferably 37% or less; more preferably 36.5% or less.

Preferably, the reaction mixture contains no monomer other than one or more monovinyl aromatic monomer and one or more multivinyl aromatic monomer.

In the method of the present invention, aqueous suspension polymerization is performed on the reaction mixture. Aqueous suspension polymerization is a process in which resin beads are produced. In the process of aqueous suspension polymerization, preferably, droplets of the reaction mixture are dispersed in water, preferably with stirring. One or more suspension stabilizers is preferably used to stabilize the droplets. Preferably, the droplets also contain one or more initiator that is insoluble in water and that is soluble in the monomer(s) in the droplet. The droplets optionally additionally contain seed particles. Seed particles are polymer particles that were formed prior to the suspension polymerization process. Preferably, the initiator decomposes to form one or more free radicals, which initiate a free-radical vinyl polymerization, converting most or all of the monomer in the droplet into polymer, forming the polymer bead. Preferably, the process of aqueous suspension polymerization converts each droplet to a resin bead. Preferably, the amount of monomer that is converted to polymerized units of polymer is, by weight based on the sum of the weights of the monovinyl aromatic monomer and the multivinyl aromatic monomer, 80% or more; more preferably 90% or more; more preferably 95% or more; more preferably 99% or more. Preferably, the polymer that is formed is water-insoluble.

Preferably, the composition of the resin beads has polymerized units of monovinyl aromatic monomer in an amount, by weight based on the weight of the resin beads, of 93.3% or more, more preferably 94% or more. Preferably, the composition of the resin beads has polymerized units of monovinyl aromatic monomer in an amount, by weight based on the weight of the resin beads, of 96% or less, more preferably 95% or less.

Preferably, the composition of the resin beads has polymerized units of multivinyl aromatic monomer in an amount, by weight based on the weight of the resin beads, of 4% or more, more preferably 5% or more. Preferably, the composition of the resin beads has polymerized units of multivinyl aromatic monomer in an amount, by weight based on the weight of the resin beads, of 7% or less, preferably 6% or less.

Preferably, after the resin beads are formed, they are separated from the water used in the aqueous suspension polymerization. Preferably, the resin beads are dried, either by heat or by washing with a water-soluble solvent that is then removed by evaporation. Preferably, the porogen is also removed from the resin beads. Preferably, porogen is removed during the drying process. If necessary, porogen may be removed by washing the resin beads with an appropriate solvent, which is subsequently removed by evaporation.

The resin beads formed by aqueous suspension polymerization are sulfonated. Sulfonation is a process in which sulfonate groups (which have the structure $—SO_3H$) are attached to the polymer. The sulfonate groups are preferably in the acid form. Preferably, the process of sulfonation includes reacting the resin beads with sulfuric acid. Preferably, sulfonation is performed after separating resin beads from the water that was used in the aqueous suspension polymerization process. Preferably, sulfonation is performed in a solvent other than water. Preferably, in the resin beads of the present invention, the quotient formed by dividing the number of moles of sulfonate groups by the number of moles of aromatic rings in the polymerized units of the resin beads is 0.8 or higher; more preferably 0.9 or higher. Preferably, in the resin beads of the present invention, quotient formed by dividing the number of moles of sulfonate groups by the number of moles of aromatic rings in the polymerized units of the resin beads is 1.2 or lower; more preferably 1.1 or lower.

Preferably, the resin beads of the present invention have BET surface area of 15 $m^2/g$ or higher; more preferably 20 $m^2/g$ or higher; more preferably 25 $m^2/g$ or higher; more preferably 30 $m^2/g$ or higher. Preferably, the resin beads of the present invention have BET surface area of 38 $m^2/g$ or lower; more preferably 35 $m^2/g$ or lower.

Preferably, the resin beads of the present invention have volume capacity (VC) of 0.7 or higher; more preferably 0.8 or higher; more preferably 0.9 or higher; more preferably 0.95 or higher. Preferably, the resin beads of the present invention have volume capacity (VC) of 2.0 or lower; more preferably 1.7 or lower; more preferably 1.3 or lower.

Preferably, the resin beads of the present invention have pore volume of 0.1 $cm^3/g$ or higher; more preferably 0.15 $cm^3/g$ or higher; more preferably 0.18 $cm^3/g$ or higher. Preferably, the resin beads of the present invention have pore volume of 0.29 $cm^3/g$ or lower; more preferably 0.25 $cm^3/g$ or lower; more preferably 0.22 $cm^3/g$ or lower.

Preferably, the resin beads of the present invention have mean pore diameter of 10 nm or more; more preferably 20 nm or more. Preferably, the resin beads of the present invention have mean pore diameter of 70 nm or less; more preferably 50 nm or less; more preferably 30 nm or less; more preferably 28 nm or less.

Preferably, the resin beads of the present invention have Moisture Hold Capacity (MHC) of 64% or higher; more preferably 69.5% or higher. Preferably, the resin beads of the present invention have MHC of 78% or lower.

Preferably, the resin beads of the present invention have Weight Capacity (Wt. Cap.) of 5.13% or higher; more preferably 5.17% or higher. Preferably, the resin beads of the present invention have Wt. Cap. of 5.3% or lower; more preferably 5.2% or lower.

Another method of assessing the porosity characteristics of a collection of resin beads is known herein as the Partitioning Test. This test is taught by S. J. Kuga, in *Journal of Chromatography*, vol. 206, pp. 449-461, 1981. Resins are, if necessary, neutralized to the $Na^+$ form and then washed with 20 mM sodium phosphate buffer solution in water. Resin is then dewatered to remove water from between the beads using humid vacuum filtration, in which air at 100% relative humidity is drawn by vacuum over the resin beads. A test solution that contains solutes of various sizes is brought into contact with the beads, and the mixture is allowed to reach equilibrium. In general, a very small solute will diffuse relatively readily into the collection of resin beads, and the supernatant solution will be depleted of that solute. Similarly, in general, a very large solute will not diffuse very readily into the collection of resin beads, and the concentration of that solute in the supernatant will remain nearly unchanged. The supernatant is analyzed by gel permeation chromatography using a 20 mM sodium phosphate buffer solution in water as the mobile phase (identical to the solution used for washing the resin), and the amount of solute of each size that diffused into the collection of resin beads is determined. From this a pore volume (in ml per gram of resin) is determined for each individual size of solute. Typically, a collection of resin beads will have pore volume of 0.5 ml/g or above for solutes of 0.5 nm or smaller. Many resins will exhibit a cutoff value, which a size above which any solute of that size will have pore volume of 0.1 ml/g or below.

A preferred use for the resin beads of the present invention is as a catalyst for a chemical reaction. Preferably, one or more reactants are reacted with each other in the presence of a plurality of the resin beads of the present invention to form one or more products. Preferred chemical reactions are aldol condensation, dehydration, alkylation of aromatics, condensation, dimerization, esterification, etherification, hydration, and combinations thereof. More preferred are dehydration, esterification, and combinations thereof. More preferred are esterification reactions having the reactants and products as follows:

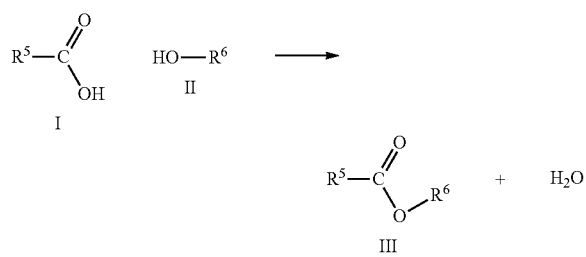

where $R^5$ and $R^6$ are organic groups. Preferably, $R^5$ is either a hydrocarbyl group or a hydrocarbyl group attached to a carboxyl group that is capable of forming an anhydride group with the carboxyl group shown in structure I. More preferably, $R^5$ is a hydrocarbyl group with 1 to 20 carbon atoms; more preferably, $R^5$ is either a hydrocarbyl group with 8 to 20 carbon atoms or is a hydrocarbyl group of structure IV

where $R^7$ is hydrogen or an alkyl group; more preferably $R^7$ is hydrogen or methyl. More preferably, $R^5$ is a hydrocarbyl group of structure IV. More preferably, $R^7$ is methyl. Preferably, $R^6$ is an alkyl group. More preferably, $R^6$ is an alkyl group having 1 to 20 carbon atoms. More preferably, $R^6$ is either an alkyl group having 8 to 20 carbon atoms or an alkyl group having 1 to 4 carbon atoms. More preferably, $R^6$ is an alkyl group having 1 to 4 carbon atoms; more preferably $R^6$ is methyl. Preferably, among embodiments in which $R^5$ or $R^6$ is a group having 8 or more carbon atoms, it is preferred that exactly one of $R^5$ or $R^6$ (but not both) is a group having 8 or more carbon atoms.

Some preferred esterification reactions are as follows:

| Acid (structure I) | Alcohol (structure II) | Ester (structure III) |
| --- | --- | --- |
| maleic anhydride | methanol | dimethyl maleate |
| lauric acid | methanol | lauric acid methyl ester |
| stearic acid | methanol | stearic acid methyl ester |
| acrylic acid | methanol | methyl acrylate |
| acrylic acid | ethanol | ethyl acrylate |
| acrylic acid | butyl alcohol | butyl acrylate |
| acrylic acid | $C_8$-$C_{20}$ alkyl alcohol | acrylic acid, $C_8$-$C_{20}$ alkyl ester |
| methacrylic acid | methanol | methyl methacrylate |
| methacrylic acid | ethanol | ethyl methacrylate |
| methacrylic acid | butyl acrylate | butyl methacrylate |
| methacrylic acid | $C_8$-$C_{20}$ alkyl alcohol | methacrylic acid, $C_8$-$C_{20}$ alkyl ester |

Also contemplated are uses for the resin of the present invention in which the resin is impregnated with a metal that is not an alkali metal or an alkaline earth. When such a metal is used, preferred are Ru, Th, Pt, Pd, Ni, Au, Ag, Cu, and mixtures thereof; more preferred are Pd, Rh, and Cu. When the resin of the present invention in which the resin is impregnated with a metal that is not an alkali metal or an alkaline earth, preferred chemical reactions conducted in the presence of the resin are hydrogenolysis, nitrate reduction, carbon-carbon couplings (for example, Heck and Suzuki reactions), oxidation, hydroformylation, and selective reduction of alkenes, ketones, alcohols, alkynes or acids.

Preferably, when the resin is used as a catalyst, the resin is not impregnated with a metal that is not an alkali metal or an alkaline earth. Preferably, the amount of metal that is not an alkali metal or an alkaline earth, by weight based on the weight of the resin, is 0.1% or less; more preferably 0.01% or less.

Preferably, the reactants and the resin beads are brought into contact with each other. For example, reactants and the resin beads may be placed into a vessel and stirred. For another example, the resin beads and the acid could be charged to the reactor and the alcohol added in semicontinuous addition until high conversion is achieved under distillation conditions for side products like water or dimethyl ether under pressure or atmospheric conditions, temperature range from 30° C. to 200° C. For another example, the process can also be a continuous flow through process where the feedstock contains the reactants, which are in contact with the resin beads in a packed bed reactor configuration. Such a continuous process can be run in temperature range of 30° C. to 200° C. (compatible with the catalyst thermal stability limits) and pressure from 0.1 to 10 MPa, with a feedstock linear hourly space velocity (LHSV) of from 0.1 to 15 ($h^{-1}$). Preferably, while the reactants are in contact with the resin beads, reactants react with each other to form the product. Preferably, the reaction is conducted at 35° C. or above; more preferably 50° C. or above. Preferably, the reaction is conducted at 130° C. or lower.

The following are examples of the present invention.

EXAMPLE 1

Methods of Aqueous Suspension Polymerization and Sulfonation to Form Resin Beads Aqueous suspension polymerization was conducted using standard techniques, using 300 g of aqueous phase (water and suspending agents), 270 g of organic phase (monomers (styrene (STY) and Divinyl Benzene (DVB), initiators and porogen). The porogen used was methyl isobutyl carbinol (MIBC) in 34-40% based on total organic phase. Typical mixing, time and temperatures were used for the synthesis steps. After polymerization, the resulting polymer beads were washed with excess water and oven dried. Sulfonation of this resin was performed by standard sulfonation methods. The result is a crosslinked poly(STY-co-DVB) sulfonated resin.

EXAMPLE 2

Conversion to Acid Form

Some commercial resins were obtained in the sodium form. Prior to use as catalyst, these resins were converted to acid form as follows. 70 mL of resin was charged to a column along with deionized water. 1 liter solution of HCl 4% (by weight) was downflowed at 250 mL/h, followed by 2 liter of deionized water at 250 mL/h. Final pH of effluent was confirmed to be within 2-3.

EXAMPLE 3

Reaction of Methanol with Methacrylic Acid 60 mL of catalyst in acid form were washed with 600 mL deionized water in a column with downflow process at 120 mL/hour. The catalyst was dried in a Buchner funnel to remove excess water and charged again into the column with MeOH. 2000 mL of methanol were flowed through the column in downflow process at 120 mL/hour. At the end of the process the catalyst was transferred as slurry in methanol to a graduated cylinder and the volume registered. The catalyst was then dried in a Buchner funnel to remove excess methanol. 150.0 g of Methanol were weighed and used to charge the catalyst and methanol to the 500 mL reactor. 40 mg of inhibitor, MEHQ, was weighed and charged to the reactor and stirred at 300 rpm for all the runs. The reactor was heated to 60° C. within 30 minutes. 40 g of Methacrylic Acid (GMAA) was charged to the reactor and the reaction held at 60° C. for 6 hours. 1 mL samples for gas chromatography were taken at the following reaction times: 10 seconds, 1 hour, 2 hour, 3 hour and 4 hour. In situ infrared measurements were started before the GMAA was charged and samples measured every 30 seconds during the 4 hour run. In situ Infrared measurements were used to follow kinetics for the runs and estimate the reaction rate observed constants.

EXAMPLE 4

Porosity Measurements by BET Method

Resin Example 11 was made as in Example 1. Resin Example 11 is a styrene/divinyl benzene copolymer with 6% DVB, made with 35% MIBC. Comparative Example C12 was made with 7% DVB and 35% MIBC as in Example 1. Also tested were Diaion™ PK-208 resin and Diaion™ PK-212 resin, from Mitsubishi Chemical; and Dowex™ CM-4 resin from Dow Chemical Company.

Samples were prepared as follows. 60 ml of resin that was wet with water was prepared in a vertical column 500 ml of methanol was flowed down through the column at 2 BV/hr, followed by 500 ml of toluene at 2 BV/hr, followed by 500 ml of isooctane at 2 BV/hr. The resin was then dried at 45° C. under vacuum for 24 hours.

Porosity included surface area (SA), total pore volume (PV), and mean diameter (diam) of the pores. The results were as follows:

| Sample | % DVB[1] | % MIBC[2] | VC[3] | SA ($m^2/g$) | PV ($cm^3/g$) | Pore diam (nm) |
|---|---|---|---|---|---|---|
| Diaion ™ PK-208 | 4 | | 1.32 | 13.28 | 0.0866 | 26.1 |
| Diaion ™ PK-212 | 6 | | 1.75 | 6.38 | 0.0304 | 19.0 |
| Dowex ™ CM-4 | 4 | note[4] | 0.65 | 26.27 | 0.2980 | 45.4 |
| Example Resin 11 | 6 | 35 | 1.23 | 32.68 | 0.2037 | 25.0 |
| Comparative Resin C12 | 7 | 35 | 1.24 | 40.02 | 0.3056 | 30.5 |

Note
[1]polymerized units of divinylbenzene, by weight based on the dry weight of polymer
Note
[2]methylisobutyl carbinol, used as porogen while making the resin, by weight based on the dry weight of the polymer.
Note
[3]Volume Capacity (meq/L)
Note
[4]The amount of porogen used in making Dowex ™ CM-4 is greater than 39% by weight based on the weight of monovinyl aromatic monomer plus the weight of multivinyl aromatic monomer.

EXAMPLE 5

Physical Toughness

Physical toughness of the resin was assessed by osmotic shock attrition (OSA), which is performed by osmotic shock attrition (OSA), which is performed by volume expansion effect of the catalysts making a column of a packed bed of the resin and then flowing the following solutions through the column: deionized water, then diluted acid (4% by weight aqueous HCl), then deionized water, then 4% by weight aqueous NaOH, and finishing with deionized water wash. 40 cycles were done, and resin breakage measured at the end of the process. The resin breakage was measured by microscope observation where 100 total beads were counted and the broken one recorded as a percent. The less physical toughness the resin had, the higher the % Breakdown.

The following styrene/divinyl benzene copolymer resins were made as in Example 1: Comparative Resins C1-C2 and Example Resins 3-5. Also tested was Diaion™ PK-212 resin, from Mitsubishi Chemical. Comparative Resins C1 and C2 are comparative because the level of MIBC is too low. Diaion™ PK-212 resin is comparative because it has BET surface area lower than 15 $m^2/g$.

These resins were tested, and the OSA results were as follows:

| Sample | % DVB[1] | % MIBC[2] | % Breakdown |
|---|---|---|---|
| Comparative Resin C1 | 6 | 0 | 47 |
| Comparative Resin C2 | 6 | 34 | 15 |
| Example Resin 3[3] | 6 | 35 | 2 |
| Example Resin 4 | 6 | 36 | 1 |
| Comparative Resin 5 | 7 | 35 | 1 |
| PK-212 | 6% | unknown | 5 |

Note
[1]polymerized units of divinylbenzene, by weight based on the dry weight of polymer
Note
[2]methylisobutyl carbinol, used as porogen while making the resin, by weight based on the dry weight of the polymer.
Note
[3]Example Resin 3 is a duplicate preparation of Example Resin 11

Comparative Resin C1 had 0% MIBC; because there was no porogen, it had very low porosity and had very high % breakdown. Comparative Resin C2 had only 34% MIBC; its porosity was still not high enough, and it had unacceptably high % breakdown. PK-212 had porosity of 6.38 m2/g (surface area), 0.0304 cm3/g (Pore volume), microporosity 0.0010 cm3/g, and 19.01 nm (Pore Diameter 4V/A) and had unacceptably high % breakdown.

EXAMPLE 6

Conversion of Methacrylic Acid to Methyl Methacrylate

The infrared measurement described above yielded the % conversion, which is the moles of methyl methacrylate produced divided by the moles of methacrylic acid present at the beginning of the reaction. The % conversion ("% Conv") is considered to be a measure of the effectiveness of the catalyst.

Samples were made as in Example 1 and tested as described in Example 3. Results were as follows ("nt" means not tested). Comparative C21 had too little DVB. Comparative C26 had too much MIBC.

| Sample | % DVB[1] | % MIBC[2] | % Conv at 2 hours | % Conv at 3 hours | % Conv at 4 hours |
|---|---|---|---|---|---|
| Comparative C21 | 3 | 36 | 60 | nt | 77 |
| Resin 22 | 4 | 36 | 60 | nt | 78 |
| Resin 23 | 5 | 36 | 61 | nt | 76 |
| Resin 24 | 6 | 36 | 57 | 67 | 76 |
| Comparative 25 | 7 | 36 | 49 | nt | 71 |
| Comparative C26 | 6 | 40 | 40 | 50 | 57 |

Note
[1]polymerized units of divinylbenzene, by weight based on the dry weight of polymer
Note
[2]methylisobutyl carbinol, used as porogen while making the resin, by weight based on the dry weight of the polymer.

The Example resins 22-24 show catalytic effectiveness superior to Comparatives C25 and C26. Example resins 22-24 show a trend that, at equal MIBC, increasing DVB leads to decreasing % conversion; from this trend, it is concluded that samples with higher levels of DVB would have even lower % conversion. Therefore it is concluded that samples with DVB of 7% or above would have unacceptably low % conversion. Comparative C21 shows acceptable catalytic effectiveness, but it also is expected to show unacceptably low physical toughness. A sample that was nearly identical to C21 was made and tested as follows:

| Sample | % DVB[1] | % MIBC[2] | % Breakdown |
|---|---|---|---|
| Comparative C27 | 3 | 35 | 33.09 |

Notes [1] and [2] as above

EXAMPLE 7

Characteristics

Various resins were made with the following characteristics. "unk" means unknown; "nt" means not tested.

| Example | % DVB | % MIBC | % MHC | Wt. Cap. | Vol. Cap. | HMPS | Density | MeOH shrink |
|---|---|---|---|---|---|---|---|---|
| 31 | 5.0 | 34.8 | 70.6 | 5.18 | 1.11 | 0.661 | 1.12 | 0.854 |
| 32 | 4.0 | 34.8 | 73.6 | 5.20 | 0.99 | 0.668 | 1.10 | 0.771 |
| C33[1] | 3.0 | 34.8 | 77.8 | 5.24 | 0.83 | 0.779 | 1.08 | 0.735 |
| C34[1] | 7.0 | 34.8 | 67.6 | 5.13 | 1.20 | 0.809 | 1.13 | 0.900 |
| C35[1] | 7.0 | 34.8 | 68.2 | 5.19 | 1.24 | 0.584 | 1.13 | 0.871 |
| PK-208[1] | 4.0 | unk | 69.0 | 5.14 | 1.19 | 0.650 | nt | 0.841 |
| PK-212[1] | 6.0 | unk | 60.4 | 5.12 | 1.57 | 0.734 | nt | 0.860 |
| PK-216[1] | 8.0 | unk | 55.0 | 5.16 | 1.85 | 0.683 | nt | 0.916 |
| PK-218[1] | 9.0 | unk | 53.5 | 5.04 | 1.88 | 0.679 | nt | 0.909 |

Note
[1]Comparative

EXAMPLE 8

Partitioning Test

Various samples were measured using the Partitioning Test. The "cutoff" size above which the pore volume drops below 0.1 ml/g is shown below:

| Example | % DVB | % MIBC | cutoff size |
|---|---|---|---|
| 31 | 5.0 | 34.8 | greater than 10 nm |
| 32 | 4.0 | 34.8 | greater than 10 nm |
| PK-208[1] | 4.0 | unk | less than 2 nm |
| PK-212[1] | 6.0 | unk | less than 2 nm |
| PK-216[1] | 8.0 | unk | less than 2 nm |
| PK-218[1] | 9.0 | unk | less than 2 nm |

Note
[1]Comparative

The invention claimed is:

1. A method of making a product of the chemical reaction of one or more reactants, said method comprising reacting said one or more reactants with each other in the presence of a plurality of resin beads, wherein said resin beads comprise
    (i) 93.5% to 96% polymerized units of monovinyl aromatic monomer, by weight based on the weight of said resin beads,
    (ii) 4% to 6.5% polymerized units of multivinyl aromatic monomer, by weight based on the weight of said resin beads,
wherein said resin beads have BET surface area of 15 to 38 $m^2/g$ and volume capacity of 0.7 or higher, wherein the chemical reaction is

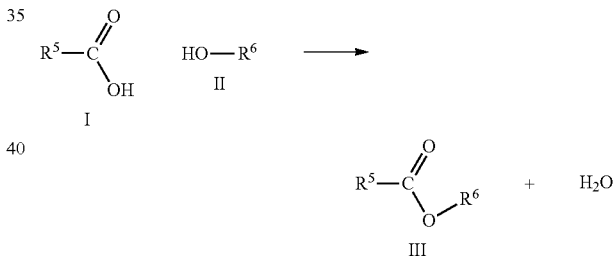

wherein $R^5$ is either a hydrocarbyl group or a hydrocarbyl group attached to a carboxyl group that is capable of forming an anhydride group with the carboxyl group shown in structure I, and wherein $R^6$ is an alkyl group.

2. The method of claim 1, wherein said product comprises a (meth)acrylate ester, and wherein said reactants comprise (meth)acrylic acid and a $C_1$ to $C_3$ alcohol.

3. The method of claim 2, wherein said (meth)acrylic acid is methacrylic acid and wherein said alcohol is methanol.

4. The method of claim 1, wherein $R^6$ is an alkyl group having 1 to 20 carbon atoms.

5. The method of claim 1, wherein $R^5$ is a hydrocarbyl group having 1 to 20 carbon atoms.

6. The method of claim 5, wherein $R^6$ is an alkyl group having 1 to 20 carbon atoms.

7. The method of claim 1, wherein $R^6$ is an alkyl group having 1 to 4 carbon atoms.

8. The method of claim 1, wherein $R^5$ is either a hydrocarbyl group with 8 to 20 carbon atoms or is a hydrocarbyl group of structure IV
IV
wherein $R^7$ is hydrogen or an alkyl group.
9. The method of claim 8, wherein $R^6$ is an alkyl group having 1 to 4 carbon atoms.
* * * * *